(12) United States Patent
Eismann et al.

(10) Patent No.: US 10,503,244 B2
(45) Date of Patent: Dec. 10, 2019

(54) OPERATION OF A DETECTOR FACILITY

(71) Applicant: Siemens Healthcare GmbH, Erlangen (DE)

(72) Inventors: Alfons Eismann, Pinzberg (DE); Alexander Graf, Forchheim (DE); Michael Grafberger, Bamberg (DE); Stefan Hartmann, Eggolsheim (DE); Thomas Hilderscheid, Altdorf (DE); Thomas Reichel, Kalsdorf bei Graz (AT)

(73) Assignee: Siemens Healthcare GmbH, Erlangen (DE)

( * ) Notice: Subject to any disclaimer, the term of this patent is extended or adjusted under 35 U.S.C. 154(b) by 203 days.

(21) Appl. No.: 15/585,521

(22) Filed: May 3, 2017

(65) Prior Publication Data

US 2017/0322619 A1    Nov. 9, 2017

(30) Foreign Application Priority Data

May 9, 2016    (DE) .......................... 10 2016 207 904

(51) Int. Cl.
*G06F 1/32*    (2019.01)
*G06F 1/26*    (2006.01)
(Continued)

(52) U.S. Cl.
CPC ............. *G06F 1/3296* (2013.01); *A61B 6/00* (2013.01); *A61B 6/03* (2013.01); *A61B 6/42* (2013.01); *A61B 6/4233* (2013.01); *A61B 6/4266* (2013.01); *A61B 6/54* (2013.01); *A61B 6/56* (2013.01); *A61B 6/58* (2013.01); *A61B 6/582* (2013.01); *A61B 6/585* (2013.01); *G06F 1/26* (2013.01); *G06F 1/266* (2013.01); *G06F 1/32* (2013.01); *G06F 1/325* (2013.01);
(Continued)

(58) Field of Classification Search
None
See application file for complete search history.

(56) References Cited

U.S. PATENT DOCUMENTS 8,822,938 B2    9/2014  Freund et al.
9,588,231 B2 *  3/2017  Graf ......................... G01T 1/175
(Continued)

FOREIGN PATENT DOCUMENTS

DE    102005014119 A1    10/2005
DE    102012204601 A1    9/2012
(Continued)

*Primary Examiner* — Tanh Q Nguyen
(74) *Attorney, Agent, or Firm* — Harness, Dickey & Pierce, P.L.C.

(57) ABSTRACT

A detector facility for a medical imaging system is described. The detector facility has a plurality of individual detectors and at least one detector controller. The detector facility is embodied such that it can be switched to at least one power-saving mode, in which at least one portion of the components of the individual detectors is deactivated and concurrently at least one portion of the components of the detector controller is not deactivated. A medical imaging system, in particular a computed tomography system, having such a detector facility; and a corresponding method for operating a detector facility of a medical imaging system are also described.

27 Claims, 4 Drawing Sheets

(51) Int. Cl.
  *G06F 1/3296* (2019.01)
  *A61B 6/00* (2006.01)
  *G06F 1/3287* (2019.01)
  *G06F 1/3234* (2019.01)
  *A61B 6/03* (2006.01)
  *G06F 1/3206* (2019.01)
  *H04N 5/32* (2006.01)
  *H04N 5/369* (2011.01)

(52) U.S. Cl.
  CPC .......... *G06F 1/3206* (2013.01); *G06F 1/3243* (2013.01); *G06F 1/3287* (2013.01); *A61B 6/032* (2013.01); *H04N 5/32* (2013.01); *H04N 5/3698* (2013.01); *Y02D 10/10* (2018.01); *Y02D 10/11* (2018.01); *Y02D 10/172* (2018.01); *Y02D 50/20* (2018.01)

(56) References Cited

U.S. PATENT DOCUMENTS

| | | |
|---|---|---|
| 2005/0207534 A1 | 9/2005 | Petrick et al. |
| 2012/0243664 A1 | 9/2012 | Nishii |
| 2016/0174928 A1 | 6/2016 | Demharter |
| 2017/0322619 A1* | 11/2017 | Eismann .............. A61B 6/4233 |

FOREIGN PATENT DOCUMENTS

| | | |
|---|---|---|
| DE | 102005049228 B4 | 3/2014 |
| DE | 102014226686 A1 | 6/2016 |

* cited by examiner

OPERATION OF A DETECTOR FACILITY

PRIORITY STATEMENT

The present application hereby claims priority under 35 U.S.C. § 119 to German patent application number DE 102016207904.2 filed May 9, 2016, the entire contents of which are hereby incorporated herein by reference.

FIELD

At least one embodiment of the invention generally relates to a detector facility for a medical imaging system, which has a number of individual detectors and at least one detector controller as well as a voltage supply for the individual detectors and the detector controller. At least one embodiment of the invention also generally relates to a medical imaging system having such a detector facility and to a method for operating a detector facility of a medical imaging system.

BACKGROUND

Detector facilities of this kind are used in computed tomography systems in particular. The individual detectors concerned are generally analog components (the individual detectors are therefore also frequently referred to as "analog frontends"), which comprise the actual detector elements, which as individual detector pixels convert the incoming X-ray radiation into electrical signals as measurement data, and at least one highly integrated analog-digital converter (ADC) and a multiplexer connected upstream of the ADC, which transfers the analog signals of the detector elements or pixels to the shared ADC. How many such individual detectors a detector facility has will depend firstly on the total number of detector elements or pixels of the detector and secondly on the number of pixels or detector elements per individual detector.

Thus, for example, there are "smaller" individual detectors comprising only 16 channels for 16 individual pixels and a shared multiplexer with an ADC connected downstream. Equally, there are also individual detectors with 64 channels or more. For a detector facility with only 64 or 128 pixels, it would therefore basically suffice to use just one or two individual detectors with 64 channels each. As a rule, however, a plurality of individual detectors is needed.

The measurement data digitalized by the ADCs is sent by the individual detectors to the detector controller, which serves not only to accept the measurement data or raw data for image reconstruction but also to control the individual detectors, i.e. to transmit corresponding control signals to the latter in order, for example, to read out the measurement data in a synchronized manner, etc. The electronics of the detector controller normally operate digitally, which is why the detector controller is usually also referred to as a "digital backend".

In order to provide the large number of pixels (customary computed tomography systems have around 50,000 pixels or even more) and the electronics for controlling the individual detectors and for transferring the relatively large quantities of data, i.e. the recorded projection data or raw data, these detector facilities need a lot of power. Depending on the detector type and number of individual detectors, a power of up to 400 watts or in individual cases even more is currently needed. The bulk of the power needed is accounted for by the individual analog detectors. Thus, these need, at a rough estimate, approx. 95% of the total power of the detector facility. As the number of pixels (and thus usually also of individual detectors) is constantly rising—computed tomography systems with more than 100,000 pixels are currently in the planning stage—it can be assumed that in future the power requirements will be even higher.

Irrespective of the current use of the medical imaging system or computed tomography system, previously the maximum power for the complete detector electronics system has always been consumed. In clinics and radiological practices, however, it can frequently arise that a computed tomography system will be operated for a prolonged period without any direct patient examination, i.e. without raw data for images currently being acquired. This period may amount to just a few minutes, for example between two scans of a patient, if the latter has to be repositioned, for example, or if other organs are to be recorded or a contrast agent has first to be administered. Between different patients, however, this period may also extend from a few hours to half a day or even overnight. In order to reduce unnecessary energy consumption during prolonged waiting periods, there has previously only been the option of shutting down the entire computed tomography system, which in turn, however, comes at the expense of the time that is needed in order to return the device to operating mode again. Shutting down the entire system is therefore not possible in many cases, in particular where it is clear that the next patient examination will take place in a foreseeable period, but also possibly overnight when e.g. emergency cases are likely.

SUMMARY

Embodiments of the present invention are directed to a detector facility, a corresponding medical imaging system and a method for operating a detector facility, in which the power requirements can be reduced.

At least one embodiment is directed to a detector facility; at least one embodiment is directed to a medical imaging system; and at least one embodiment is directed to a method for operating a detector facility.

The detector facility according to at least one embodiment of the invention has a number (i.e. at least one, but preferably a plurality) of individual detectors, in particular in the form of the above-described analog frontends, and a detector controller, in particular in the form of the above-described digital backend. This detector controller may, however, also comprise a plurality of sub-units or modules, which, for example, are assigned to groups of individual detectors and are coupled to a shared unit in order in turn to coordinate the groups among one another. The unit concerned is, however, preferably an individual detector controller, to which all the individual detectors are connected. The individual detectors and the detector controller each have, as is customary, a plurality of components such as, for example, an operational amplifier, sample-and-hold elements, analog multiplexer ADCs etc. in the individual detectors or controllers, power supply units etc. in the detector controller. The the detector controller is embodied such that it can be switched to at least one power-saving mode in which at least one portion of the components of the individual detectors is deactivated and concurrently at least one portion of the components of the detector controller is not deactivated.

A medical imaging system according to at least one embodiment of the invention, which is preferably a computed tomography system, is equipped with such a detector facility according to at least one embodiment of the invention.

A method, according to at least one embodiment of the invention for operating a detector facility of a medical imaging system of at least one embodiment of the aforementioned type, includes an aspect wherein, after switching over to a power-saving mode, at least one portion of the components of the individual detectors is deactivated and concurrently at least one portion of the components of the detector controller is not deactivated.

Further particularly advantageous designs and further developments of the invention will emerge from the dependent claims and the description below, it also being possible for the independent claims of one claim category to be developed further in a manner analogous to that of the dependent claims of another claim category and for the features of various example embodiments to be combined to form new example embodiments.

BRIEF DESCRIPTION OF THE DRAWINGS

The invention will be described once again in detail below with reference to the attached figures with the aid of example embodiments. The same components in the various figures are labeled with identical reference numbers.

DETAILED DESCRIPTION OF THE EXAMPLE EMBODIMENTS

Figure 1:
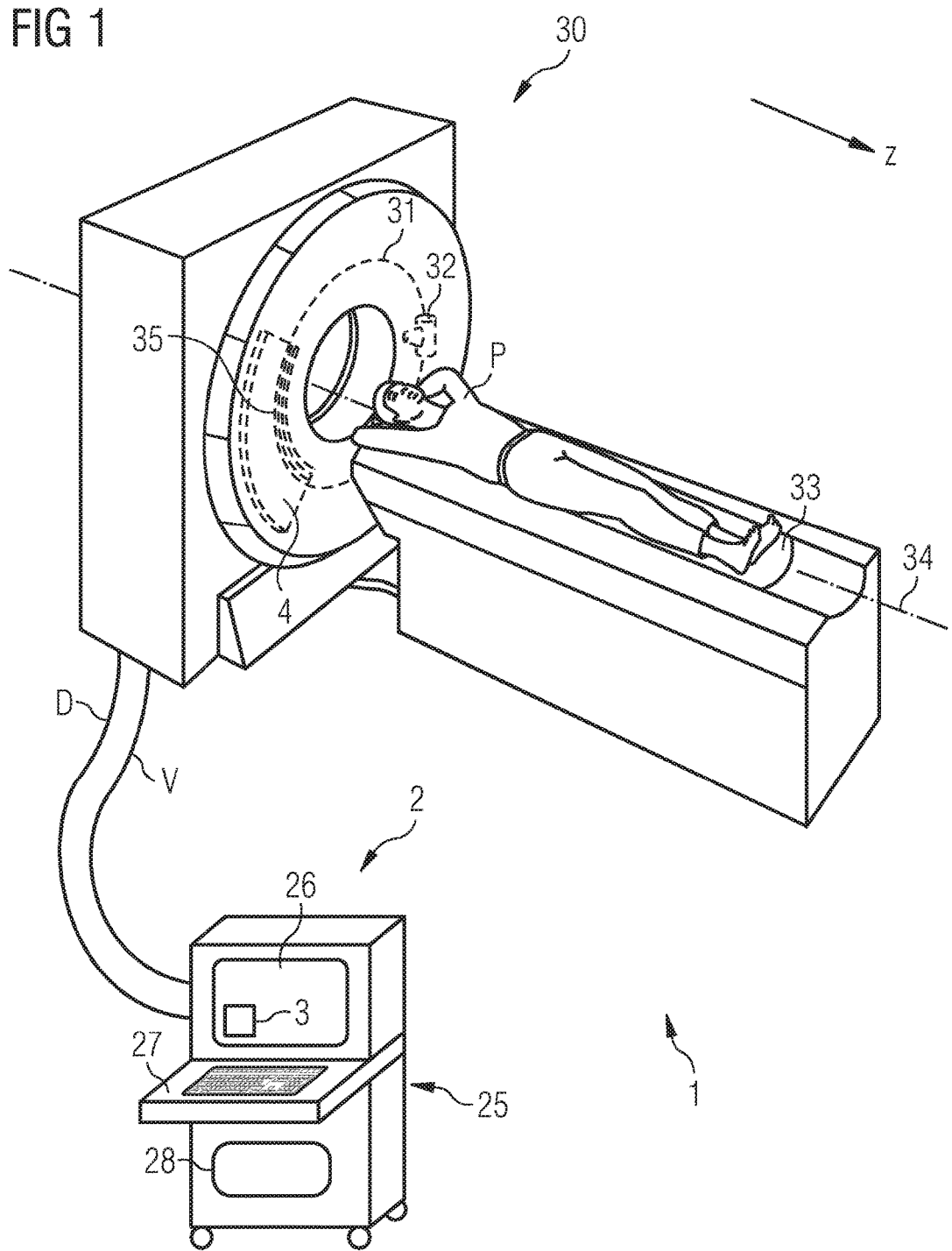
FIG. 1 shows an outline schematic representation of an example embodiment of a computed tomography system according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The detector facility according to at least one embodiment of the invention has, as described in the introduction, a number (i.e. at least one, but preferably a plurality) of individual detectors, in particular in the form of the above-described analog frontends, and a detector controller, in particular in the form of the above-described digital backend. This detector controller may, however, also comprise a plurality of sub-units or modules, which, for example, are assigned to groups of individual detectors and are coupled to a shared unit in order in turn to coordinate the groups among one another. The unit concerned is, however, preferably an individual detector controller, to which all the individual detectors are connected. The individual detectors and the detector controller each have, as is customary, a plurality of components such as, for example, an operational amplifier, sample-and-hold elements, analog multiplexer ADCs etc. in the individual detectors or controllers, power supply units etc. in the detector controller.

According to at least one embodiment of the invention, this detector facility is now embodied such that it can be switched to at least one power-saving mode, in which at least one portion of the components of the individual detectors is deactivated and concurrently at least one portion of the components of the detector controller is not deactivated. If, in particular, the components of the individual detectors that operate analogically and consume particularly high levels of energy (such as, for example, the operational amplifiers and/or sample-and-hold elements and/or multiplexers and/or ADCs) are deactivated when they are not needed, considerable amounts of energy can be saved in total.

Since in the detector controller (i.e. the digital backend), key components remain active even in power-saving mode, the full performance capability of the medical imaging system can nonetheless be established at any time considerably faster than if the entire system is shut down. This is due, in particular, to the fact that a) the firmware of the controllers on the digital backend does not have to be reconfigured,
b) the training sequence for the transfer of data within the different subcontrollers (which can e.g. have the functions of correctly activating the frontend modules, correctly configuring the frontend modules, collecting the data which comes from the frontend modules and converting it into a defined protocol) does not have to executed again in order to ensure secure data transfer,
c) the data interface of the detector with the imaging computer does not have to be checked again for correct and error-free data transfer,
d) the control and communication network does not have to be established and verified again,
e) the existing and stored calibration data in the digital backend electronics does not have to be regenerated for the analog frontends and stored again.

The medical imaging system can therefore—unlike previously—not only be switched on and off, but in switched-on mode can additionally be switched back and fore between at least one such power-saving mode and another operating mode (referred to hereinbelow as "scanning mode"), in which raw data can be acquired.

How much energy is actually saved will depend on which components are deactivated and which remain active in power-saving mode. How fast the detector facility can be switched back from power-saving mode to scanning mode again will in turn depend on this. If the individual detectors are completely deactivated, as will be explained later, up to 95% of the energy can be saved in power-saving mode. If only parts of the individual detectors are deactivated, in order, for example, to be able to switch back to scanning mode particularly quickly, for example up to 75% of the energy can be saved.

At the same time, it is in principle also possible to combine various power-saving modes, i.e. for example in short pauses of just a few minutes, [the detector facility] is switched to a first power-saving mode, in which only some particularly high-energy-consuming components of the individual detectors are deactivated, but from which the facility can be switched back to scanning mode in a few seconds, and in longer pauses, which are to be expected, the individual detectors are fully deactivated, for example, in a second power-saving mode. At the same time it is also possible for the facility to be switched, where applicable, between the various power-saving modes. However, considerable energy can essentially be saved even if only one power-saving mode is available.

A medical imaging system according to at least one embodiment of the invention, which is preferably a computed tomography system, is equipped with such a detector facility according to an embodiment of the invention.

A method according to at least one embodiment of the invention for operating a detector facility of a medical imaging system of the aforementioned type is characterized in that after switching over to a power-saving mode at least one portion of the components of the individual detectors is deactivated and concurrently at least one portion of the components of the detector controller is not deactivated.

With the aid of at least one embodiment of the invention, it is therefore possible to reduce drastically the power intake of the medical imaging system outside actual patient examination operating mode and consequently to provide a system that as a whole is energy-saving. Another advantage is that the generation of heat by the detector facility is on average lower, as in the standby periods no power is consumed by the individual detectors and emitted in the form of waste heat. Consequently, additional savings can be made in terms of energy for cooling the detector facility. The reliability of the detector facility is also increased as the average operating temperature is lowered as a result.

Further particularly advantageous designs and further developments of the invention will emerge from the dependent claims and the description below, it also being possible for the independent claims of one claim category to be developed further in a manner analogous to that of the dependent claims of another claim category and for the features of various example embodiments to be combined to form new example embodiments.

In a particularly preferred embodiment, the detector facility is embodied such that certain components of the detector controller which are not needed in power-saving mode are also deactivated in power-saving mode. This also means that the detector controller is then deactivated insofar as only those components which are needed in power-saving mode continue to remain active. Besides components which, as will be explained later, are needed in order to switch back out of power-saving mode, these components, which are also needed in power-saving mode, are, for example, one or more controllers, which receive the switching signals for switching on/off from system control and themselves in turn generate these switching signals. Components that can be switched off, on the other hand, include, for example, the measurement data generating unit, the synchronization unit, the monitoring unit for the individual detectors and the communication unit within the detector controller.

Where, as explained later for a preferred example embodiment, the detector facility is embodied such that it permits a switchover to various power-saving modes, for example to a first power-saving mode for short pauses and a particularly fast switch back to scanning mode and to a second power-saving mode for longer pauses, this variant is preferably used only in the second power-saving mode, as switching off components of the detector controller may involve taking somewhat more time switching back to scanning mode.

In order to switch over to a power-saving mode, the individual detectors may preferably each have a deactivation device. This deactivation device may be embodied in order to deactivate certain components (i.e. for example the analog components described above) of the individual detector concerned, e.g. by outputting a suitable deactivation command. This procedure is particularly suitable for switching over to a power-saving mode from which it is possible to switch back very quickly to scanning mode.

The deactivation device may comprise, for example, an interpreter unit in an input/output interface (I/O interface) of the individual detector, which interprets certain commands which come from the detector controller and/or a system control of the imaging system appropriately as commands or signals for switching over to power-saving mode or for switching back to scanning mode. These may also be common commands which are already being transmitted to the individual detectors, such as for example a "scan-preload command", which is normally sent by the system control in order to prepare a scan, and which is then followed a short time (e.g. 1 to 2 s) later by a "make-data signal", which initiates the actual data acquisition. This make-data signal is usually active while data is being acquired. Switching off the make-data signal can in turn be interpreted as a signal or event for switching over to power-saving mode and deactivating the relevant components of the individual detector.

A detector facility also normally has a voltage supply arrangement for the individual detectors and the detector controller. This comprises, for example, one or more power supply units with a network connection e.g. to the power supply network, which is provided externally, and a corresponding line network within the detector facility for distributing electric power to the components of the detector controller and to the individual detectors. This voltage supply arrangement is preferably for the most part integrated in the detector controller, with, for example, one or more power supply units and the corresponding lines (e.g. in the form of conductor tracks, cables, plugs or similar) being integrated in the detector controller and connections being provided for the individual detectors. In principle, however, it could also be embodied in a separate unit, to which the individual detectors and the detector controller are connected via corresponding voltage supply lines.

The voltage supply arrangement preferably has at least one switching mechanism and is embodied such that in a first switching state of this switching mechanism, which corresponds to a power-saving mode (or power-saving switching state), the voltage supply to the individual detectors is interrupted and at the same time the voltage supply for the detector controller continues to be maintained. In this power-saving mode, the power requirements can be reduced to a very small fraction, for example—as explained above— to around 5% or less, as the voltage supply to the individual detectors can be switched separately from the voltage supply to the control electronics and consequently in power-saving mode the individual detectors are no longer supplied with any power at all.

In a particularly preferable embodiment of this procedure, the voltage supply arrangement and/or the switching mechanism are embodied such that in the first switching state of the switching mechanism (i.e. in power-saving mode) the voltage supply for certain components of the detector controller which are not needed in power-saving mode is interrupted. This means that it is precisely here—as explained above— that the voltage supply for the control unit is maintained only insofar as the components which are needed in power-saving mode continue to be supplied.

The switching mechanism can be implemented in various ways. Preferably, however, the switching mechanism is integrated in the detector controller, i.e. embodied as part of the latter.

The switching mechanism preferably comprises at least one switch unit and a switch control unit for controlling the switch unit. These components are preferably each also part of the detector controller.

The switching mechanism is particularly preferably embodied such that in the first switching state at least the voltage supply for the switch unit(s) and the switch control unit is maintained, as these units will be used for switching back from standby mode to full operating mode.

There are also various options for implementing the switch unit(s). Essentially, this could involve separate switches, such as for example one or more MOSFETs or an arrangement of a plurality of switches, interposed in the power supply lines. The switch inputs of these switches may be activated e.g. by the switch control unit. In order to keep the number of switches low, it is advantageous to arrange these for example upstream of any distribution nodes, if for example a plurality of individual detectors are supplied with voltage from the same output of a power supply unit.

In a variant which is constructed with as few additional components as possible and is therefore preferable, the voltage supply arrangement comprises at least one power supply unit, preferably a plurality of power supply units, each with at least one supply voltage input, an integrated switch unit and a supply voltage output, as well as a deactivation input for inputting a deactivation signal for the supply voltage output. Via this deactivation input, the integrated switch unit of the power supply unit can thus be switched with the aid of the deactivation command such that no more supply voltage is available at the supply voltage output concerned. It is possible here for a plurality of supply voltage outputs to be switched simultaneously via a deactivation input or for a separate deactivation input to be available for each supply voltage input. Such a deactivation input, hereinafter also referred to as an "enable input", is then connected to the switch control unit and receives from the latter the deactivation signal for deactivating the relevant supply voltage output(s), such that the voltage supply to the individual detectors connected thereto is interrupted and is consequently switched over to standby mode.

This deactivation signal (which could also be referred to as a deactivation command) may for example be simply a logical switching state of a switch output of the switch control unit. By switching back the switch output of the switch control unit, the deactivation signal can then also be canceled again, such that the integrated switch units in the power supply units again cancel the voltage supply interruption and the supply voltage is again present at the supply voltage outputs and is thereby switched back to full operating mode. Equally, however, it would also be possible for a special reactivation command to be sent from the switch control unit to the power supply unit or units, for example again to the deactivation input or to one or more separate activation inputs in order to switch over again from standby mode to full operating mode.

To function, the individual detectors may each need some detector operating data, in particular calibration data or correction values. Such calibration data or correction values serve e.g. to compensate for hardware-dependent differences in sensitivity of the various individual detectors. This calibration data is firstly determined in a calibration procedure during initial commissioning of the detector facility or imaging system and can then be stored in a system control of the imaging system. During operation, the detector operating data, in particular calibration data, is held available in suitable memories of the individual detectors, such that the individual detectors can work using these values. The calibration procedure can be performed again at certain intervals, for example during maintenance of the system, in order to update the data. Besides the calibration data or correction values, there is also other detector operating data which is stored in an appropriate manner and can be held available in each case in the memories of the individual detectors for their respective operation, such as for example detector operating data or configuration data which specifies which measurement range is being used (whether, for example, a high-dose or low-dose recording is involved), it being possible for the sensitivity of the respective individual detectors to be adjusted with the aid of the detector operating data, or detector operating data which influences the readout speed at the individual detectors, etc.

The detector facility preferably comprises a suitable detector-operating-data-administration unit, which is embodied for sending initially detector operating data, preferably calibration data, to the individual detectors, after the voltage supply has been switched on again. The appropriate detector operating data can be taken, for example, from the memory of the system control of the medical system, i.e. for example the computed tomography control, or the system control can be prompted to transmit this detector operating data—as when completely switching the entire system on again—to the individual detectors. The detector-operatingdata-administration unit is connected for this purpose via a data link to the individual detectors and the switch control unit, in order to accomplish this task in synchronization with the switchover from standby mode to full operating mode, i.e. to ensure that the individual detectors receive the respective detector operating data.

In a particularly preferable embodiment, the detector facility has a detector-operating-data-administration unit of a type such that, before the switching mechanism switches over to the first switching state, i.e. before the switchover to standby mode, detector operating data, preferably the abovementioned calibration data, is read out from the individual detectors and, having been assigned to the individual detectors, stored in a memory. This memory is particularly preferably a separate memory which is different from the memory in which the system control of the medical system has stored this data. When the voltage supply to the individual detectors is switched on again, i.e. when switching back from standby mode to full operating mode, the detector operating data can then be sent back again from this memory to the individual detectors. The detector-operating-data-administration unit can consequently be the same detector-operating-data-administration unit that also ensures that the detector operating data is sent to the individual detectors again. Reading out the detector operating data from the individual detectors independently of the system control before switching over to standby mode and storing this operating data for the individual individual detectors in a separate memory specifically provided/reserved for this purpose, as well as sending it back to the individual detectors after switching back from standby mode with the aid of a separate detector-operating-data-administration unit has the advantage that the switching mechanism can operate completely self-sufficiently, i.e. without intervening in the system control of the medical system. It should be noted that the system control itself is a highly complex system and that the stand-alone detector-operating-data-administration unit with its own memory, which can preferably also be part of the switching mechanism or at least of the detector controller, can considerably reduce the outlay on the inventive embodiment of the detector facility. This separate memory can preferably be a memory that is integrated for example in the detector controller. Basically, however, another memory area, which is easily accessible to the detector-operating-data-administration unit but is jointly used by other components, can also be used.

As mentioned above, in a preferred variant, various power-saving modes can be combined with one another. In this case, deactivation of (only) certain components of an individual detector can, with the aid of the deactivation device of the individual detector, particularly preferably be effected automatically when data acquisition is terminated. This may, for example, take place, as described above, when the make-data signal is canceled. Preferably, the power-saving mode is then equally automatically canceled again and switched back to scanning mode upon a scan command, for example upon receipt of the scan-preload signal, such that the detector facility is immediately ready upon receipt of the subsequent make-data signal to acquire raw data.

Switching over to another power-saving mode, in which a voltage supply to the individual detectors is fully interrupted and therefore even more power is saved, is on the other hand preferably initiated deliberately by the user via a command from a user interface, when a longer pause is pending. This power-saving mode is then preferably also canceled again via a user interface.

FIG. 1 shows by way of example and in outline schematic form an inventive embodiment of a computed tomography system 1, which comprises a computed tomography device 30 and a system control 2 with a user terminal 25.

The system control 2 is shown here as a unit that is separate from the computed tomography device 30 and connected to the latter via lines. In principle, however, it can also be integrated fully or partially in the computed tomography device 30.

The computed tomography device 30 comprises a patient table 33 for positioning a patient P as an examination object P, the patient table 33 being adjustable along a system axis 34 such that the patient P is movable in and through the measuring field. The system axis 34 is also referred to as the z-axis.

The computed tomography device 30 comprises furthermore in the customary manner a gantry 31 having a source-detector arrangement 32, 4 rotatably mounted about the system axis 34. The source-detector arrangement has an X-ray radiation source 32 and a detector facility 4, which, lying opposite one another on the gantry 31, are oriented such that, during operation, X-ray radiation originating from the focus of the X-ray radiation source 32 through the measuring field (which is defined by space between X-ray radiation source 32 and detector facility 4, which the X-ray radiation radiates through) strikes the individual detectors of the detector facility 4. The individual detectors of the detector facility 4 are structured in individual pixels, which are arranged in a plurality of detector rows and columns. The individual detectors are arranged spatially such that they offer a contiguous pixelated detector surface 35, which the X-ray radiation strikes, such that projection data can be measured in a spatially resolved manner. The electronic structure of the detector facility 4 will be explained in detail below with the aid of FIGS. 2 and 3.

Such a computed tomography system 1 is used, as is known, for 3D image reconstruction. To record image data from an examination area (or a "region of interest" in the inside of the examination object P, e.g. an area with a certain organ) projection data is recorded from a plurality of different projection directions during rotation of the source-detector arrangement. In the case of a so-called "spiral scan", for example, during a rotation of the source-detector arrangement, the patient table 33 is simultaneously continuously moved in the direction of the system axis 34. The X-ray radiation source and the detector consequently move in this type of scan on a helical path about the patient P. In a "sequential scan" by contrast, projection data is recorded each time the patient table 33 comes to a standstill at various positions along the system axis 34.

The projection data represents the intensity values of the X-ray radiation, attenuated by the patient P, measured at the individual pixels. The projection data is sent as so-called raw data via a data channel D to the system control 2, which has an image reconstruction device 28, in which, based on the raw data, the image data from the inside of the patient P can be reconstructed in the customary manner. This can then be represented e.g. on a display unit 26 of the user terminal 25 and/or stored in a memory and/or sent to other systems. The user terminal 25 comprises furthermore inter alia a keyboard 27 as input device, by which an operator can optionally set values for parameters, in particular for the recording of raw data and/or the image reconstruction. Via this user terminal 25, the operator can input, as will be described hereinbelow, for example a command for switching over to a particular power-saving mode, hereinafter called "standby mode", or for switching back out of this standby mode.

Via a supply line V, the computed tomography device 30—and therefore also the detector facility 4—is supplied with the required operating voltage or the required electric power. In FIG. 1, this supply line V runs to the system control 2, which in turn is connected to a suitable power supply network in the clinic or practice (not shown). In principle, however, the computed tomography device 30 could also itself be connected to a suitable power supply network. This will depend e.g. on what components are present in the computed tomography device 30 for converting the voltage supplied by the power supply network into the voltages needed by the components of the computed tomography device 30.

As already explained in the introduction, a drawback in existing known computed tomography systems is that in order to maintain fast operational readiness, the computed tomography system together with all its components has to be permanently supplied with the required (maximum) electric power, which is also needed during raw data acquisition.

In order to greatly reduce this energy use, the detector facility 4 here is embodied such that in a first power-saving mode (hereinafter also referred to as "acquisition standby mode") certain components of the individual detectors 20a, 20b, 20c, 20d . . . 20m (analog frontend) can be automatically deactivated if they are not currently needed for data acquisition, and, furthermore, the voltage supply to the individual detectors 20a, 20b, 20c, 20d . . . 20m and the voltage supply to the detector controller 5 (digital backend) needed for this purpose can be controlled separately, in order, in a second power-saving mode, the above-mentioned standby mode, in which even more power is saved, to switch off the individual detectors 20a, 20b, 20c, 20d . . . 20m completely from the voltage supply.

Figure 2:
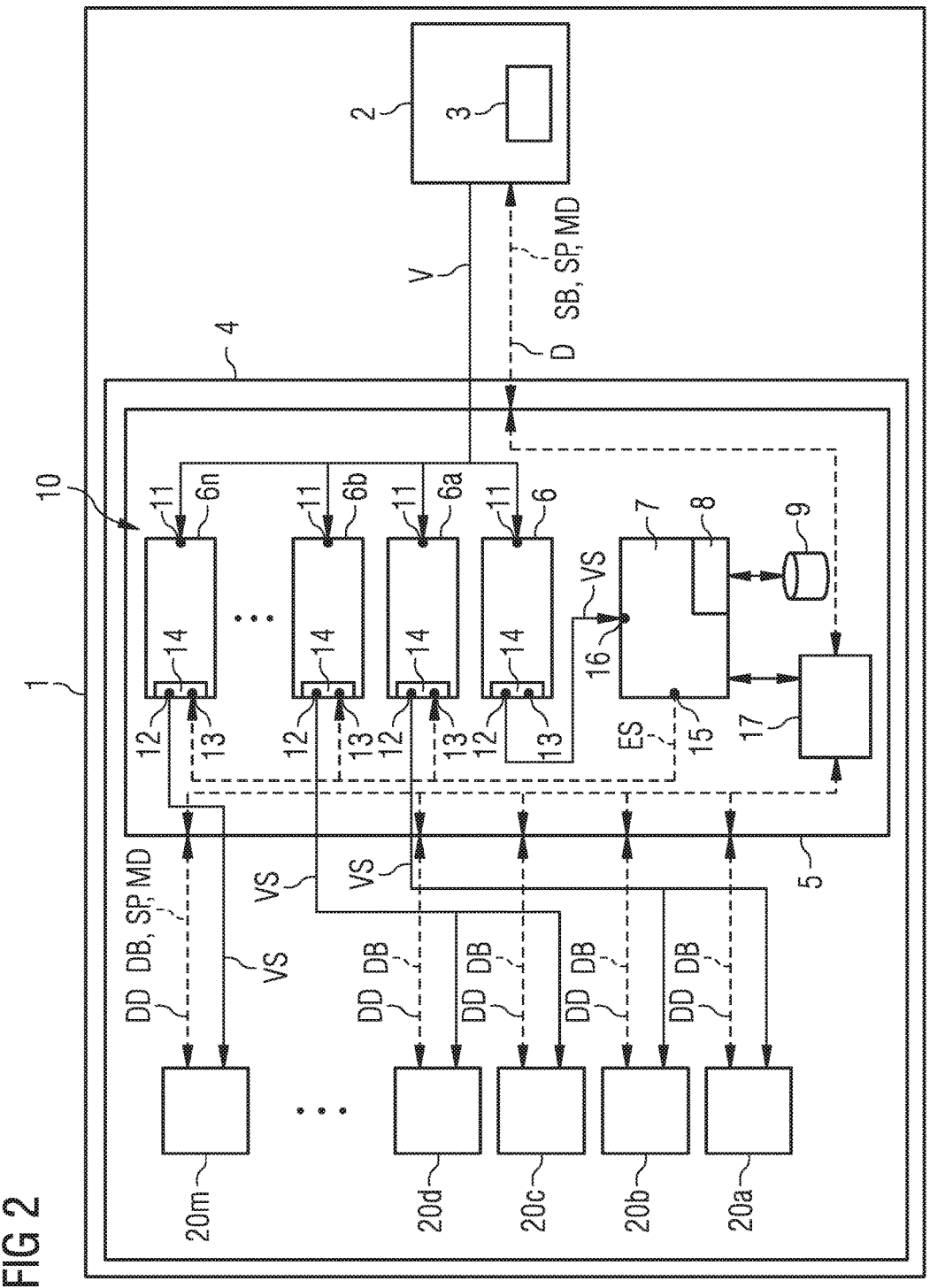
FIG. 2 shows a partial block diagram of an example embodiment of a detector facility according to the invention.
Figure 3:
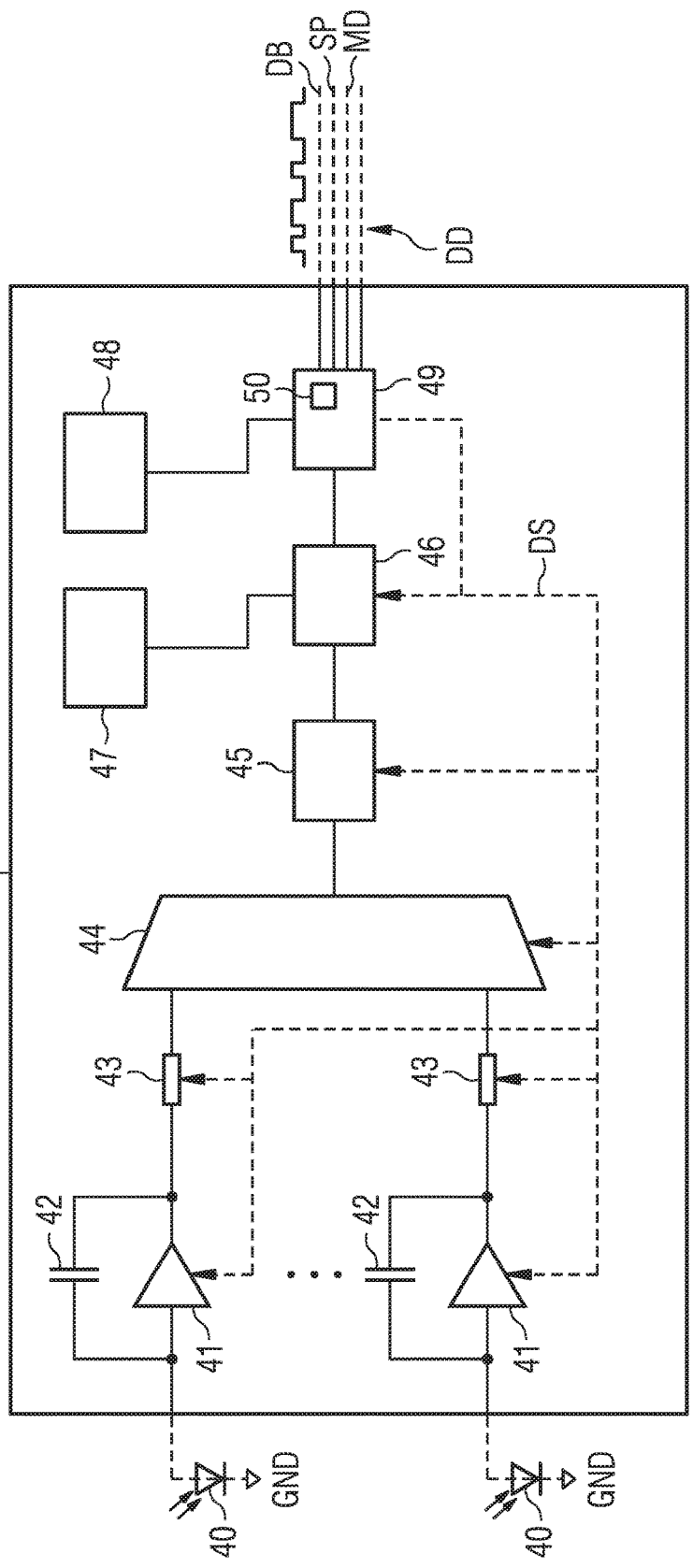
FIG. 3 shows a partial block diagram of an example embodiment of an individual detector of the detector facility according to FIG. 2.

A detector facility 4 design suitable for this purpose is shown in FIGS. 2 and 3, in each case in the form of partial block diagrams, the components that are particularly relevant to an embodiment of invention being shown, for the sake of simplicity, only in outline schematic representation.

FIG. 2 shows the detector facility 4 with the detector controller 5 and a plurality of individual detectors 20a, 20b, 20c, 20d, . . . , 20m connected thereto. The detector controller 5 is in turn connected via the supply voltage line V and a data channel D to the system control 2 of the computed tomography system 1. In turn, only those components of the detector controller 5 are represented schematically that are required for operation in accordance with an embodiment of the invention with the option of separate disconnection of the voltage supply to the individual detectors 20a, 20b, 20c, 20d, . . . , 20m. It is clear that this detector controller 5 also has all the other components which customary detector controller have. Likewise, the individual detectors 20a, 20b, 20c, 20d . . . 20m in FIG. 2 are represented only in outline schematic form as individual blocks. A more precise schematic representation of the design of the individual detectors 20a, 20b, 20c, 20d, . . . , 20m can be seen in FIG. 3.

Each of the individual detectors 20a, 20b, 20c, 20d, . . . , 20m comprises a number of photodiodes 40, which form the individual detector elements or pixels of the individual detectors 20a, 20b, 20c, 20d, . . . , 20m. The incidence of X-ray radiation on the photodiodes generates an electrical signal in the usual manner. The photodiodes 40 here are merely representative of any type of radiation converters that will convert X-ray radiation into electrical signals. Such an individual detector 20a, 20b, 20c, 20d, . . . , 20m may have, for example, 16, 32, 64, 128 or even more pixels.

The photodiodes 40 are each connected to ground GND and, to record the electrical signal generated by the incidence of the X-ray radiation, are connected to an operational amplifier 41, to which a capacitor 42 is connected in parallel in the usual manner. At the output of the operational amplifier 41 there is in each case located in the usual manner a sample-and-hold element 43. The outputs of these sample-and-hold elements 43 are each connected to a shared multiplexer 44 for all the pixels or detector channels. This multiplexer 44 reads out sequentially the signals of the individual detector channels and sends all the signals in a chronological multiplex procedure to an analog-digital converter (ADC) 45. This converter then forwards the digitalized measurement data to a pre-processing unit 46, which for example corrects the measurement data using specified calibration data which is stored in a memory 47 and factors in the sensitivities for the individual pixels and performs further precalculations, such as for example reformatting the data into a particular data transfer protocol.

The individual detectors 20a, 20b, 20c, 20d, . . . , 20m are each connected via data channels DD to the detector controller 5. Via these data channels DD, the raw data can be sent from each of the individual detectors 20a, 20b, 20c, 20d, . . . , 20m to the detector controller 5 and conversely control data, in particular detector operating data DB, e.g. calibration data DB, can also be received or sent. The connection of the individual detectors 20a, 20b, 20c, 20d, . . . , 20m to the data channel DD is in each case via an input/output interface 49. In a further memory 48, configuration data which is used by the input/output interface 49 can be stored. This input/output interface 49 also receives via the data channel DD certain commands for controlling the various components of the individual detector 20a, 20b, 20c, 20d, . . . , 20m concerned, in particular the previously mentioned scan-preload signal SP for preparing the detector for data acquisition, and the make-data signal MD, upon which data acquisition takes place and the individual signals of the photodiodes 40 are read out and processed as described.

The data channels DD are connected in the detector controller 5 here, for example, to an internal controller 17, which on the other side is connected in turn via a data channel D to the system control 2 and thus forwards the data from the individual detectors 20a, 20b, 20c, 20d, . . . , 20m to the system control 2 and vice versa. It is clear that, instead of an individual controller 17, a plurality of controllers can also be used in parallel here and/or that the controller 17 can include a plurality of partial controllers and optionally further components.

In addition, the individual detectors 20a, 20b, 20c, 20d, . . . , 20m are each supplied with the necessary voltage by the detector controller 5. To this end, the individual detectors 20a, 20b, 20c, 20d . . . 20m are each connected as previously mentioned via supply lines VS to the detector controller 5. The connection on the part of the individual detectors 20a, 20b, 20c, 20d . . . 20m is again achieved here via the input/output interface 49. However, there can also be a separate voltage supply interface present. The detector controller 5 has furthermore a voltage supply arrangement 10, which comprises inter alia a plurality of power supply units 6a, 6b, . . . , 6n. Each of these power supply units 6a, 6b, . . . , 6n has a supply voltage input 11, a supply voltage output 12 and an "enable input" 13, i.e. a deactivation input 13. Located in each of the power supply units 6a, 6b . . . 6n is an internal switch unit 14, which is embodied such that, if a particular voltage potential is set at the enable input 13, i.e. a particular logical switching state is achieved, the associated supply voltage output 12 is deactivated, i.e. no voltage is applied there.

The power supply units 6a, 6b, ..., 6n are connected by way of their supply voltage inputs 11, for example by way of the supply line V, to the system control 2 and are supplied from there with an input voltage of 12V. At each of the supply voltage outputs 12, the supply voltage of 5V needed for the individual detectors 20a, 20b, 20c, 20d, ..., 20m is output. However, it is explicitly pointed out that these voltages are only examples and that in principle other voltage combinations are also possible.

The power of the individual power supply units 6a, 6b, ..., 6n is in each case sufficient for a plurality of individual detectors 20a, 20b, 20c, 20d, ..., 20m to be connected to a supply voltage output 12. In the example embodiment shown in FIG. 2, these are in each case two individual detectors 20a, 20b, 20c, 20d, ..., 20m connected to a supply voltage output 12 of a power supply unit 6a, 6b, ..., 6n.

The voltage supply arrangement 10 additionally comprises here, besides the controller 17, a switch control unit 7, which is arranged, for example, in the form of a microcontroller or the like likewise in the detector controller 5, e.g. on the same board on which the power supply units 6a, 6b, ..., 6n are also located. The controller 17 and the switch control unit 7 are coupled to one another here via a data link and/or can communicate with one another.

This switch control unit 7 has a switch output 15, hereinafter referred to as an "enable output" 15, via which an enable signal ES can be given to the enable inputs 13 of the power supply units 6a, 6b, ..., 6n, to which the individual detectors 20a, 20b, 20c, 20d, ..., 20m are connected. In other words, this switch control unit 7 is embodied such that, to switch over to the above-mentioned standby mode, as an enable signal ES at the enable output 15 the logical voltage level is applied that is needed in order to deactivate the associated supply voltage outputs 12 via the enable inputs 13 of the power supply units 6a, 6b, ..., 6n. The switch control unit 7 therefore forms together with the switching mechanisms 14 in the individual power supply units 6a, 6b, ..., 6n the switching mechanism for switching over from a full operating mode to a standby mode, wherein the individual detectors 20a, 20b, 20c, 20d, ..., 20m are no longer supplied with the operating voltage needed.

In order to ensure that at least also in standby mode the required components of the detector controller 5 continue to be supplied with voltage, the detector controller 5 is equipped with at least one additional power supply unit 6, which can for example be designed in the same way as the other power supply units 6a, 6b, ..., 6n. In other words, this power supply unit 6 also has a supply voltage input 11, which is connected to the supply voltage line V to the system control 2, and a supply voltage output 12, at which the supply voltage needed for the further components of the detector controller 5, for example again 5V, is output.

Shown here as an example is a scenario in which a supply voltage input 16 of the switch control unit 7 is connected to the supply voltage output 12 of this power supply unit 6. The controller 17 is likewise supplied by this power supply unit 6 (not shown explicitly). Unlike in the case of the power supply units 6a, 6b, ..., 6n provided for the individual detectors 20a, 20b, 20c, 20d, ..., 20m, however, here the enable input 13 is not connected to the enable output 15 of the switch control unit 7. Consequently also, upon switchover to standby mode, the supply voltage output 12 of this power supply unit 6 is not disconnected, and the switch control unit 7, the controller 17 and further components of the detector controller 5, which are supplied with the supply voltage via this output, are not deactivated. Of course, besides the power supply unit 6 shown, there may be also further power supply units present which supply other components of the detector controller 5 that are not to be switched off in standby mode with the necessary voltage and which likewise are not deactivated via the enable signal ES.

To activate the enable signal ES, i.e. in order to bring the enable output 15 of the switch control unit 7 to the appropriate switching state, a "standby command" SB can simply be sent from the system control 2 via the data channel D to the detector controller 5. For this purpose, the system control 2 can have a standby activation interface 3, for example in the form of a software component, by which an appropriate window is displayed on the display device 26 of the user interface 25, and the operator can give the appropriate standby command for switching over to standby mode via an input device 27 using either a keyboard or a mouse (not shown) or another pointing device. In an analogous manner, the user can also input an appropriate command in order to switch back out of standby mode, whereby the individual detectors 20a, 20b, 20c, 20d, ..., 20m are again supplied with the necessary operating voltage. In the case shown in FIG. 2, the standby command SB, and correspondingly also the command to switch back out of standby mode, is transmitted by the system control 2 firstly to the controller 17 of the detector controller 5, which then forwards this command to the switch control unit 7.

In order to operate, the individual detectors 20a, 20b, 20c, 20d, ..., 20m usually need certain detector operating data DB, which in each case is stored in one or more memories 47, 48 (see FIG. 3) of the individual individual detectors 20a, 20b, 20c, 20d, ..., 20m. This includes, inter alia, calibration data DB, which is used to compensate for the different sensitivities of the individual detectors 20a, 20b, 20c, 20d, ..., 20m, and configuration data for the individual detectors. These memories 47, 48 in the individual detectors 20a, 20b, 20c, 20d, ..., 20m are normally volatile memories, i.e. when the supply voltage is disconnected, the contents of the memories are lost.

This detector operating data for the individual detectors 20a, 20b, 20c, 20d, ..., 20m is always stored in the system control 2. This means that, when [the facility] is switched on again from standby mode to full operating mode, the required detector operating data, in particular calibration data DB, could be transmitted from there via the detector controller 5 to the individual detectors 20a, 20b, 20c, 20d, ..., 20m. This could be prompted by the switch control unit 7 or else synchronously with the standby command SB by the system control 2 itself. In order, however, in one implementation of the inventive switching mechanism to intervene as little as possible in the complex system of the system control 2, the switch control unit 7 in the preferred example embodiment shown in FIG. 2 has a detector-operating-data-administration unit 8 with a separate memory 9. The detector-operating-data-administration unit 8 and the memory 9, like the other components of the switch control unit 7, continue to be supplied with the necessary voltage even in standby mode, i.e. are not switched off.

The detector-operating-data-administration unit 8 can be used to ensure that the detector operating data DB, in particular calibration data DB, from the memories 47, 48 of the individual detectors 20a, 20b, 20c, 20d, ..., 20m is additionally stored in the memory 9. This can be done either once after a recalibration or a respecification of detector operating data DB to the individual detectors 20a, 20b, 20c, 20d, ..., 20m, or else automatically each time before a switchover is to be made to standby mode. After a switch back from standby mode to full operating mode, the detector operating data DB can be retrieved from the memory 9 and written back to the memories 47, 48 of the individual detectors 20*a*, 20*b*, 20*c*, 20*d*, . . . , 20*m*.

As, understandably, some time is needed for this recovery of the calibration data DB and consequently for getting the individual detectors 20*a*, 20*b*, 20*c*, 20*d*, . . . , 20*m* fully ready for a scan (in the case of a 64-channel detector about 8 to 10 s), such a switchover to standby mode is not always appropriate in the case of shorter pauses, for example in the waiting times between two scans, when the patient is only being repositioned briefly. In order also to save power in these short pauses (as even these short pauses can, over a day of operation, naturally add up to a very long period in total), there is the option here of automatically switching over to the first power-saving mode, the above-mentioned acquisition standby mode. In contrast to standby mode, this switchover occurs only inside the individual detectors 20*a*, 20*b*, 20*c*, 20*d*, . . . , 20*m*, which is why in this respect the reader is referred once again to FIG. 3.

The individual detectors 20*a*, 20*b*, 20*c*, 20*d*, . . . , 20*m* have for this purpose an interpreter unit 50, for example as part of the input/output interface 49. This interpreter unit 50 can interpret certain commands which the individual detector 20*a*, 20*b*, 20*c*, 20*d*, . . . , 20*m* receives via the detector controller 5 from the system control 2 and output a deactivation signal DS, in order to deactivate certain components of the individual detector 20*a*, 20*b*, 20*c*, 20*d*, . . . , 20*m* concerned, so that they consume no more power.

In the example embodiment shown in FIG. 3, this deactivation signal DS works in particular for the operational amplifiers 41, the sample-and-hold elements 43, the multiplexer 44, the analog-digital converter 45 and the preprocessing unit 46, as these components need the most power and can readily be disconnected from the power supply. In particular, the input/output interface 49 with the interpreter unit 50 and the memories 47, 48 with the calibration data DB and configuration data are not affected by the deactivation signal DS, as these are to continue to work unchanged and in particular also the calibration data DB is to remain stored locally.

The effect of the deactivation signal DS is shown here only schematically as a line to the individual components affected. This is actually any signal to disconnect the components concerned from the power supply, for example a power supply to the components concerned can simply be interrupted with this signal DS via one or more suitable switches.

In the particular case, quite specific typical signals of the system control 2 are used to trigger the deactivation or activation of the components. These are firstly the scan-preload signal SP, which is emitted by the system control 2 shortly before a scan so that on the one hand the X-ray source and on the other the detector are prepared for a subsequent scan. This scan-preload signal SP is output when the operator actuates the X-ray release on the user interface of the system control 2. Approx. 1 to 2 s are needed in any case from actuation of this X-ray release until the actual emission of X-ray radiation. The actual make-data signal MD which ensures that from the time of reception of this make-data signal MD at the individual detectors 20*a*, 20*b*, 20*c*, 20*d*, . . . , 20*m* the raw data is acquired, i.e. the photodiodes 40 are read out as described, therefore follows synchronously with the release of radiation approx. 1 to 2 s later (i.e. in accordance with the time which the X-ray source needs in order to emit the X-ray radiation). This make-data signal MD remains active until such time as there is no more data to be read out. The deactivation of this make-data signal MD can therefore be interpreted by the interpreter unit 50 such that the deactivation signal DS is then output in order to disconnect the specified components from the power supply. Conversely, the scan-preload signal SP can be used to switch the power to the components on again, i.e. to cancel the deactivation signal DS.

Figure 4:
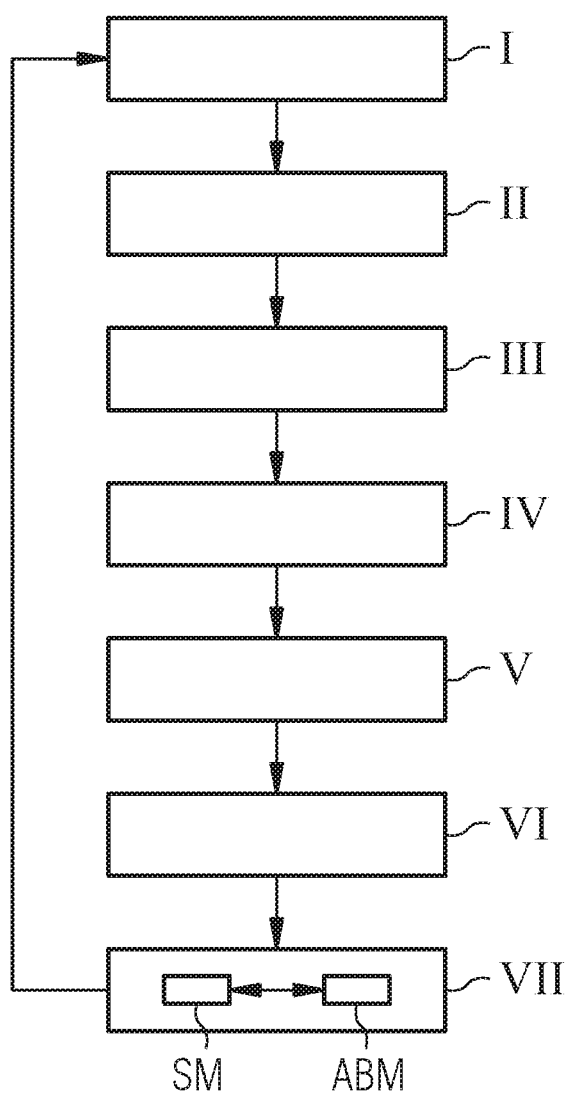
FIG. 4 shows a flow diagram of an embodiment of a method according to the invention.

The above-mentioned preferred procedure for switching over to standby mode and back is described once again with reference to the flow diagram in FIG. 4.

In step I, the detector controller 5 and the switch control unit 7 respectively receive a standby command SB from the standby activation interface 3 of the system control 2 via the data channel D. Thereupon, in step II, the detector-operating-data-administration unit 8 of the switch control unit 7 firstly ensures that the detector operating data DB is read out from the individual memories of the individual detectors 20*a*, 20*b*, 20*c*, 20*d*, . . . , 20*m* and stored in the separate memory 9. The enable output 15 of the switch control unit 7 is then switched over, i.e. an enable signal ES is output and the power supply units 6*a*, 6*b*, . . . , 6*n* of the individual detectors 20*a*, 20*b*, 20*c*, 20*d*, . . . , 20*m* are thus deactivated via the enable inputs 13 and their voltage supply thus interrupted (step III).

In step IV, there is a period of waiting until a full-operating-mode-activation signal is given again to the detector controller 5 and the switch control unit 7 respectively via the standby activation interface 3. When such a full-operating-mode-activation signal is then received, in step V, the deactivation of the supply voltage outputs 12 of the power supply units 6*a*, 6*b*, . . . , 6*n* of the individual detectors 20*a*, 20*b*, 20*c*, 20*d*, . . . , 20*m* is firstly canceled again, i.e. the interruption of the voltage supply to the individual detectors 20*a*, 20*b*, 20*c*, 20*d*, . . . , 20*m* is canceled again. In step VI, with the aid of the detector-operating-data-administration unit 8, the operating control data DB or calibration data DB is sent again to the individual detectors 20*a*, 20*b*, 20*c*, 20*d*, . . . , 20*m*, so that the entire computed tomography system 1 is fully ready to operate.

Cancelling the voltage supply interruption and sending back the calibration data to the individual detectors 20*a*, 20*b*, 20*c*, 20*d*, . . . , 20*m* requires less than 10 s. This is considerably faster than the time that is needed to establish full operational readiness when completely restarting the computed tomography system (needs approx. 5 min.).

"Full operational readiness" of the detector facility 4 is understood in the case of the example embodiment described here to mean an operating state as represented in the final method step VII in FIG. 4, i.e. the detector facility 4 is either in acquisition standby mode ABM, in which the above-mentioned components of the individual detectors 20*a*, 20*b*, 20*c*, 20*d* . . . 20*m* are still deactivated, or in scanning mode SM, in which all the components are active and data can be acquired. The operating state of the detector facility 4 is then thus determined automatically by signals from the system control, for example the above-mentioned scan-preload signal SP and the make-data signal MD. If the detector facility 4 is in acquisition standby mode ABM, the user can switch the facility to standby mode again at any time by way of a standby command SB, which is shown in FIG. 4 by a loop to method step I.

With the aid of the detector facility modified according to an embodiment of the invention, it is thus possible to reduce drastically the overall energy requirements of the imaging system, particularly if the system is not used for imaging for a prolonged period, but only has to remain ready to operate. In this period, a reduction in the power intake of 95% is perfectly possible.

In conclusion, it is once again pointed out that the control devices described in detail hereinabove are only example embodiments, which may be modified in a wide variety of ways by one skilled in the art without departing from the scope of the invention. In particular, it is also possible for the detector facility to be designed such that only one of the above-described power-saving modes can be activated. Equally, its use is not restricted to individual detectors which are designed in the manner explained above in the example embodiment, but the design can also be completely different, for example with counting X-ray detectors, which of course then also have to have components adapted thereto for accepting and processing the data. The key factor is simply that in the inventive method components which need a particularly large amount of energy can be deactivated in the individual detector when they are not used. Furthermore, the use of the indefinite article "a" or "an" does not rule out the possibility that the features concerned may also be present more than once. Nor is the possibility ruled out that elements of embodiments of the present invention shown as individual units may include a plurality of interacting subcomponents, which may optionally also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector facility, comprising:
    a plurality of individual detectors, each of the plurality of individual detectors including a plurality of first components; and
    at least one detector controller including a plurality of second components, the at least one detector controller configured to
        switch the detector facility to at least one power-saving mode in which
            at least one portion of the plurality of first components are deactivated, and
            at least one portion of the plurality of second components are not deactivated,
        switch the detector facility away from the at least one power-saving mode such that the at least one portion of the plurality of first components are reactivated, and
        transfer detector operating data to the plurality of individual detectors from a memory external to the plurality of individual detectors after the detector facility has been switched away from the at least one power-saving mode.

2. The detector facility of claim 1, wherein at least some of the plurality of second components not used in the at least one power-saving mode, are deactivated in the at least one power-saving mode.

3. The detector facility of claim 1, wherein each respective individual detector among the plurality of individual detectors includes a deactivation device configured to deactivate one or more components among the at least one portion of the plurality of first components in the respective individual detector.

4. The detector facility of claim 1, further comprising:
    a voltage supply arrangement including at least one switching mechanism configured to implement a first switching state corresponding to the power-saving mode by,
        interrupting a voltage supply to the plurality of individual detectors, and
        permitting a voltage supply to the detector controller.

5. The detector facility of claim 4, wherein the at least one switching mechanism is integrated in the at least one detector controller.

6. The detector facility of claim 4, wherein the at least one switching mechanism comprises at least one switch unit and a switch controller configured to control the at least one switch unit.

7. The detector facility of claim 6, wherein the at least one switching mechanism is configured to permit at least a voltage supply for the at least one switch unit and the switch controller in the first switch state.

8. The detector facility of claim 6, wherein the voltage supply arrangement includes at least one power supply unit including
    at least one supply voltage input,
    an integrated switch unit,
    a supply voltage output, and
    a deactivation signal input, the deactivation signal input connected to the switch controller.

9. The detector facility of claim 4, wherein the at least one detector controller is configured to transfer the detector operating data from the plurality of individual detectors to the memory before switching the detector facility to the at least one power-saving mode.

10. A medical imaging system, comprising the detector facility of claim 1.

11. A method performed by at least one detector controller included in a detector facility of a medical imaging system, the at least one detector controller configured to switch the detector facility to a power-saving mode and switch the detector facility away from the power-saving mode, the detector facility including a plurality of individual detectors, the method comprising:
    deactivating at least one portion of a plurality of first components of the plurality of individual detectors based on switching the detector facility to the power-saving mode, at least one portion of a plurality of second components of the at least one detector controller not being deactivated based on switching the detector facility to the power-saving mode;

reactivating the at least one portion of the plurality of first components based on switching the detector facility away from the power-saving mode; and transferring detector operating data to the plurality of individual detectors from a memory external to the plurality of individual detectors after the reactivating.

12. The method of claim 11, wherein the deactivating deactivates the at least one portion of the plurality of first components using at least one deactivation device included in one or more of the plurality of individual detectors.

13. The method of claim 11, wherein the deactivating deactivates the at least one portion of the plurality of first components by interrupting a voltage supply to one or more of the plurality of individual detectors while permitting a voltage supply to the at least one portion of the plurality of second components.

14. The method of claim 12, wherein the power-saving mode is a standby mode in which a voltage supply to the plurality of individual detectors is interrupted, and the deactivating deactivates the at least one portion of the plurality of first components using at least one deactivation device in response to termination of data acquisition by the medical imaging system, and initiation of switchover to the standby mode in response to an external command.

15. The method of claim 11, further comprising:

transferring detector operating data from the plurality of individual detectors to the memory before the deactivating.

16. The detector facility of claim 2, wherein each respective individual detector among the plurality of individual detectors includes a deactivation device configured to deactivate one or more components among the at least one portion of the plurality of first components in the respective individual detector.

17. The detector facility of claim 2, further comprising:

a voltage supply arrangement including at least one switching mechanism configured to implement a first switching state corresponding to the power-saving mode by, interrupting a voltage supply to the plurality of individual detectors, and permitting a voltage supply to the detector controller.

18. The detector facility of claim 17, wherein the at least one switching mechanism is integrated in the at least one detector controller.

19. The detector facility of claim 17, wherein the at least one switching mechanism comprises at least one switch unit and a switch controller configured to control the at least one switch unit.

20. The detector facility of claim 5, wherein the at least one switching mechanism comprises at least one switch unit and a switch controller configured to control the at least one switch unit.

21. The detector facility of claim 1, wherein the detector operating data is calibration data.

22. A medical imaging system, comprising the detector facility of claim 4.

23. The medical imaging system of claim 10, wherein the medical imaging system is a computed tomography system.

24. The medical imaging system of claim 22, wherein the medical imaging system is a computed tomography system.

25. The method of claim 12, wherein the deactivating deactivates the at least one portion of the plurality of first components by interrupting a voltage supply to one or more of the plurality of individual detectors while permitting a voltage supply to the at least one portion of the plurality of second components.

26. The method of claim 13, wherein the power-saving mode is a standby mode in which a voltage supply to the plurality of individual detectors is interrupted, and the deactivating deactivates the at least one portion of the plurality of first components using at least one deactivation device in response to termination of data acquisition by the medical imaging system, and initiation of switchover to the standby mode in response to an external command.

27. The method of claim 15, wherein the detector operating data is calibration data.

* * * * *